United States Patent
El Mogy

(12) 
(10) Patent No.: US 6,846,499 B2
(45) Date of Patent: Jan. 25, 2005

(54) MEDICAL EFFECT OF JOJOBA OIL

(75) Inventor: Nabil Sadek El Mogy, Cairo (EG)

(73) Assignee: Natoil & Sedico, Cairo (EG)

(*) Notice: Subject to any disclaimer, the term of this patent is extended or adjusted under 35 U.S.C. 154(b) by 96 days.

(21) Appl. No.: 10/189,888

(22) Filed: Jul. 3, 2002

(65) Prior Publication Data

US 2003/0008022 A1 Jan. 9, 2003

(51) Int. Cl.$^7$ .............................................. A61K 35/78
(52) U.S. Cl. ...................................... 424/776; 424/725
(58) Field of Search ................................ 424/776, 725

(56) References Cited

U.S. PATENT DOCUMENTS

| | | | | | |
|---|---|---|---|---|---|
| 4,585,656 | A | * | 4/1986 | Rosenthal et al. | 424/195.17 |
| 4,759,798 | A | * | 7/1988 | von Nostitz | 106/35 |
| 5,981,499 | A | * | 11/1999 | Hau | 514/29 |
| 6,365,131 | B1 | * | 4/2002 | Doshi et al. | 424/49 |
| 6,582,736 | B2 | * | 6/2003 | Quezada | 424/742 |
| 2001/0046526 | A1 | * | 11/2001 | Greenfelder | 424/779 |

FOREIGN PATENT DOCUMENTS

| | | | |
|---|---|---|---|
| DK | 169887 B | * | 3/1995 |
| JP | 07188045 A | * | 7/1995 |

OTHER PUBLICATIONS

Stampf et al. Gyogyszereszet. 1983. vol. 27, No. 3, pp. 93–95, DRAUGU Abstract enclosed.*

* cited by examiner

Primary Examiner—Christopher R. Tate
(74) Attorney, Agent, or Firm—Adam Sacharoff; Much Shelist

(57) ABSTRACT

In accordance with the present invention Jojoba Oil may be used in accordance with the treatment of and preventative measures associated with Gynecology of Obstetrics and general surgery, as well as in the treatment of eye diseases, inflammation of the internal, middle or external ear, rheumatic pain and arthritis, gingivostomatitis, toothache and dermal diseases. Jojoba oil is a natural product and is characterized by being non-irritant and non-allergic to skin and mucous membrane. This oil has lubricant, moisturizing and soothing properties, as well as having anti-bacterial, anti-inflammatory and anti-oxidant properties. It has a very high healing power and improves blood circulation, and also has high penetration into stratum corneum.

2 Claims, No Drawings

MEDICAL EFFECT OF JOJOBA OIL

FIELD OF THE INVENTION

The present invention relates to various medical effects of the Jojoba oil.

CROSS-REFERENCE TO RELATED APPLICATIONS

This application claims the foreign priority to Egyptian Patent Application No. 750 and filed on Jul. 7, 2001.

BACKGROUND OF THE INVENTION

Jojoba oil is used in Lubricating motors and added to some cosmetic preparations. However, such previous uses of Jojoba Oil are not related to the new uses subjected to this invention.

SUMMARY OF THE INVENTION

In accordance with the present invention Jojoba Oil may be used in accordance with the treatment of and preventative measures associated with Gynecology of Obstetrics and general surgery, as well as in the treatment of eye diseases, inflammation of the internal, middle or external ear, rheumatic pain and arthritis, gingivostomatitis, toothache and dermal diseases.

Moreover, the Jojoba Oil is preferably extruded in accordance with the present invention.

Numerous other advantages and features of the invention will become readily apparent from the following detailed description of the invention and the embodiments thereof, from the claims, and from the accompanying drawings.

DETAILED DESCRIPTION OF THE EMBODIMENTS

While the invention is susceptible to embodiments in many different forms, there are shown in the drawings and will be described herein, in detail, the preferred embodiments of the present invention. It should be understood, however, that the present disclosure is to be considered an exemplification of the principles of the invention and is not intended to limit the spirit or scope of the invention and/or claims of the embodiments illustrated.

Natural Jojoba oil is extracted from seeds of Jojoba shrub {Simmondsia Chinensis (LINK) Schnieder}. It is made up of straight chain esters of mono-unsaturated long chain fatty acids and fatty alcohols and has an average total carbon chain length of 42 carbons, so it is classified chemically as a liquid wax.

Jojoba oil is composed entirely of esters of high molecular weight, straight chain mono-ethylenic acids and mono-ethylenic alcohols. The unsaturated acids are mixture of eicosanoic (C20) and docosanoic (C22), with small quantities of palmiloleic (C18) and oleic (C16) acids. The unsaturated alcohols are a mixture of eicosanol and docosanol, with smaller quantities of hexacosanol and alcohols of lower molecular weight.

Jojoba oil is non-volatile and free from rancidity, and this is attributed in part to presence of tocopherols (natural anti-oxidant) as a minor constituent and mainly to its wax structure (It has only one alcohol group, so it is not subject to oxidation and will never become rancid). Furthermore, researches showed that Jojoba oil possesses the six general factors which increase permeation into stratum cornium:—
low viscosity, high unsaturation, low saponification number, short carbon chain length, low lecithin (Jojoba oil has no lecithin), straight chain molecule and branched esters.

Jojoba oil helps to avoid the two important causes of premature aging of the skin:—dryness and lipid perioxidation. It serves as an excellent non-occlusive moisturizing agent that enhances the flexibility and suppleness of the skin. At the same time, its exceptional non-tacky spread and lubricity leave a rich velvety after-feel.

Jojoba oil is characterized by having 50% of its content as insaponifiables (Triterpene alcohols and Phytosterols) while other vegetable oil contain only 2–3%. Moreover applying insaponifiables to skin increases elastin formation, which in turn increases skin luster, elasticity and integration. Jojoba Oil also provides skin protection as it has anti-allergic properties, disinfectant, and produces cell stimulation, skin regeneration and stops inflammation. The pH of Jojoba oil is balanced and reveals beneficial effects for dry and damaged skin.

Jojoba oil is also proven to have anti-inflammatory and anti-microbial effects as well. Five of the most common bacteria including staphylococcus aureus and pseudomonas aeruginosa as well as fungus candida albicans are not able to grow in Jojoba oil.

One novel way to extract the Jojoba Oil from the Jojoba seeds is as follows. First, it has been determined that the Jojoba seeds contain 50–55% of its weight oil. The Jojoba oil is extracted in phase one by pressing the Jojoba seeds under pressure reaching gradually from 1 to 35–38 Ton/Inch. About 26–28% oil from the seeds weight is obtained form the first pressing phase, also called phase one oil, which may be used for medical application. After separating the phase-one oil from the crashed seeds, the residual squeezed seeds are pressed again under pressure up to 100 Ton/Inch, which extracts second phase oil, which may be used in cosmetic and other fields. Also called second phase oil. Independently, the first-phase-oil and second-phase-oil are elutriated for certain time. The elutriated oils are then passed through 4-level filter and again elutriated for a predetermined time. The oils are refiltered through 4-level filter and a higher than the first 4-level filter, to obtain the final oil for use. The extracted oil in the first phase is superior to the ordinary oil especially in the medical effect.

The extracted Jojoba oil is effectively used in the treatment of the following:

Dermal Diseases:

It has been effectively used with salicylic acid in the treatment of psoriasis, dandruff, acne and fish skin disease. It has been effectively used with zinc oxide in the treatment of napkin dermatitis, skin rash, allergic dermatitis and monilial infection. It has been effectively used with the treatment of insect bites and the treatment of fungal infect in toes. It is effective in protecting skin from non-infective allergic materials such as liquid washing soap. It has been effectively used in treatment of mange, treating first degree burns and sun burns as well as protecting skin from hazards of ultra violate rays during sun-tanning. It is also elective as a first aid for wounds and treating inflammatory wounds and enhancing healing by primary intention. It is effective in the treatment of bedsores. It has been used in assisting treatment of alopecia areata and rogenetica. It has been used to eliminate hair lice. It has been effectively used in treatment of Herpes simplex labialis (cold sores). It has also been effectively used in healing diabetic wounds especially diabetic foot.

Treatment of Gingivostomatitis and Toothache:

The extracted Jojoba oil has been effectively used with lidocaine in the treatment of recurrent aphthous ulceration. It has been used in toothpaste to treat gingivitis and improve the circulation of gingiva. It has been effectively used with zinc oxide in temporary filling. It has also been effectively used in the treatment of the dry socket as a side effect of chemotherapy and radiotherapy.

Rheumatic Pain and Arthritis:

The Jojoba Oil is effective in treating and reliving pains of polyarthitis, rheumatic pains, arthralgia, and spondylitis. It is effective in enhancing the effect of physiotherapy and supporting body to regain its physical ability in addition to eliminating the stress and cramps.

Inflammation of the Ear

It has been effective in treatment of otitis externa and otitis media.

Treatment of Eye Diseases:

It has been effectively used in treatment of thrombosis.

General Surgery:

It has been effectively used as suppositories in treatment of acute and chronic anal fissure and anal fistula, as well as the treatment of prostatits, Hiemorroids (at $2^{nd}$ degree) and early stages of Varicose Vein.

Gynecology of Obstetrics:

It has been effectively used as a Vaginal suppository in treatment of vaginitis, used in reliving the pain accompanied with dysmenorrhoea, and used in the treatment of nipple crakes and improve its healing.

The Method of Use

The Jojoba oil is used by being added to other medicines, for achieving better effects of the novel medicine without any side effects. Examples are as following:

1—10% of Jojoba oil by weight, and 0.5% of Lidocaine hydrochloride by weight are used for treating the inflammation of mucous membrane of mouth and condition resulted form administration of antibiotics for long time.

2—50% of Jojoba Oil by weight, and 2% salicylic acid by weight are used in ointment form for treating acne, psoriases, dandruff, sebum (abnormal excessive exudatation of sebaceous glands in skin) and fish skin disease (Thick epidermis being tough and continually scalling)

3—50% of Jojoba oil by weight with 8% of zinc oxide weight can be used in treating conditions of skin rash and allergic dermatitis.

4—As suppository contain, 20% of Jojoba oil by weight can be used to treat the anal fissure.

5—Vaginal suppository containing 20% of Jojoba oil by weight can be used in treating non-infective vaginitis.

Jojoba oil is extracted by pressing the crashed seeds gradually under pressure form 1 to 35–38 Ton/Inch to obtain first phase oil, then meal well be crashed again and pressed under pressure up to 100 Ton/Inch to obtain second phase oil, then each type of oil will go through different levels of filtration, since the first phase oil is used for medical application for treating many illnesses.

As mentioned previously, from seeds, Jojoba oil and its derivatives are extracted including straight chains of mono-ethylenic acids and mono ethylenic alcohols; further more Jojoba oil is non-volatile, not subject to oxidation and not liable to rancidity in addition to its high penetrability to skin as a result of its low viscosity, high unsaturation, low saponification number, short carbon chain length, low lecithin, straight chain molecule and branched esters.

As motioned previously, the Jojoba oil is used as anti-bacteria, skin protective, anti-allergic, anti-inflammatory, anti-fungal, improving wound healing and blood circulation in the skin.

As mentioned previously, Jojoba oil as an essential element, is used for treating many dermal diseases.

As mentioned previously, Jojoba oil is used as an essential element, in the treatment of the inflammation of mucus membrane of the mouth, temporary filling and dry sockets.

As mentioned previously, Jojoba oil is used as a main element in treating and reliving pains of polyarthitis, rheumatic pains, arthralgia, and spondylitis.

As mentioned previously, Jojoba oil is used as a main element, for treating otitis externa and otitis media.

As mentioned previously, as a main element, Jojoba oil is used in treatment of thrombosis.

As mentioned previously, as a main element, Jojoba oil is used in treatment of some general surgeries such as anal fissure, anal fistula, prostatits, and Hiemorroids (at $2^{nd}$ degree).

As mentioned previously, Jojoba oil is used as a main element in treatment of vaginitis, and nipple crakes in addition to reliving the pain accompanied with dysmenorrhoea.

As mentioned previously, compound contain 10% of Jojoba oil by weight and 0.5% of lidocaine hydrochloride by weight, is particularly effective in treating mouth ulcer and gingivostomatitis and removing the erythena in addition to reducing Edema associated to these inflammations—this effect returns to the Jojoba oil properties as anti-bacterial and anti-inflammation substance. Also, the Jojoba oil acts as a painkiller for the conditions. Some of the Jojoba oil's indications are: gingivostomatitis and conditions resulted from using antibiotics for long time. Moreover, this compound has no side effects.

As mentioned previously, preparation contains 50% of Jojoba oil by weight and 2% of salicylic acid by weight and is used for treating acne, psoriasis dandruff sebum (abnormal) excessive exudatation of seba ceous glands in skin and fish skin disease; it could also be used in treatment of fungal infection as tinia (tinea). This preparation also has no side effect.

As mentioned previously, a suppository containing 20% jojoba oil by weight can be used to treat the anal fissure. It could relieve the intensity of pains and the complications in many patients as well as eliminating pills. Moreover, this suppository has no side effects.

As mentioned previously, ointments containing 50% of Jojoba oil by weight with 8% of zinc oxide by weight used in treating condition of rash, napkin dermatitis, skin inflammation, insect bytes, monilyases, and nipple fissure, no side effects have been resulted from this preparation.

As mentioned previously, a vaginal suppository containing 20% Jojoba oil by weight is used to eliminate the vaginitis (acute or recurrent). This suppository has no side effects.

Form all the above mentioned benefits, it becomes clear that Jojoba oil, in its all forms and cases, all the illnesses treated with it, has not any side-effects on the human body or environment.

From the foregoing and as mentioned above, it will be observed that numerous variations and modifications may be effected without departing from the spirit and scope of the novel concept of the invention. It is to be understood that no limitation with respect to the specific methods and apparatus illustrated herein is intended or should be inferred. It is, of course, intended to cover by the appended claims all such modifications as fall within the scope of the claims.

What is claimed is:

1. A method of treating mouth diseases by applying a composition to an affected area that includes Jojoba oil extruded from Jojoba seeds wherein the extraction of Jojoba oil is prepared by pressing a Jojoba seed under pressure from approximately 1 to approximately 38 tons/inch to obtain a first phase oil, elutriating said first phase oil for a predetermined amount of time, filtering said elutriated oil with at least a level four filter creating a filtered oil, re-elutriating said filtered oil for a predetermined amount of time creating a re-elutriated oil, and re-filtering said re-elutriated oil through a at least a level 4 filter, and wherein said composition includes at least 100% a Jojoba Oil by weight and approximately 0.5% Lidocaine Hydrochloride by weight.

2. A method of treating gingivostomatitis, aphthous ulceration, gingivitis, and the circulation or gingival, edema associated to gingivostomatitis, aphtous ulceration and gingivitis, dry socket, and erythema by topically applying to the affected area an effective amount of a composition comprising at least 10/% Jojoba Oil by weight and approximately 0.5% Lidocaine Hydrochloride by weight.

* * * * *